United States Patent
Proelss et al.

(10) Patent No.: US 8,163,079 B2
(45) Date of Patent: Apr. 24, 2012

(54) PLATELET-SHAPED, COPPER-CONTAINING, METALLIC EFFECT PIGMENTS, PROCESS FOR PREPARING THEM AND USE THEREOF

(75) Inventors: Dieter Proelss, Schwabach (DE); Ralf Deinzer, Neuhaus (DE); Wolfgang Herzing, Neunkirchen am Sand (DE); Andreas Kroell, Velden (DE); Stefan Trummer, Nürnberg (DE); Michael Becker, Lauf (DE); Katrin Wczasek, Nürnberg (DE)

(73) Assignee: Eckart GmbH (DE)

( * ) Notice: Subject to any disclaimer, the term of this patent is extended or adjusted under 35 U.S.C. 154(b) by 0 days.

(21) Appl. No.: 12/992,911

(22) PCT Filed: May 28, 2009

(86) PCT No.: PCT/EP2009/003793
§ 371 (c)(1),
(2), (4) Date: Feb. 1, 2011

(87) PCT Pub. No.: WO2009/152941
PCT Pub. Date: Dec. 23, 2009

(65) Prior Publication Data
US 2011/0179971 A1 Jul. 28, 2011

(30) Foreign Application Priority Data
May 28, 2008 (EP) .................................. 08009699

(51) Int. Cl.
*C09C 1/62* (2006.01)
*C09C 1/66* (2006.01)
*C09D 5/36* (2006.01)
*C09D 7/12* (2006.01)
*C09D 11/02* (2006.01)
*A61K 8/11* (2006.01)
*A61Q 1/02* (2006.01)

(52) U.S. Cl. ....... 106/480; 106/31.9; 428/402; 428/403; 428/457

(58) Field of Classification Search .................. 106/480, 106/31.9; 428/402, 403, 457
See application file for complete search history.

(56) References Cited

U.S. PATENT DOCUMENTS

| 2,002,891 A | 6/1931 | Hall |
| 3,995,815 A | 12/1976 | Megelas |
| 4,172,720 A | 10/1979 | Megelas |
| 4,884,754 A | 12/1989 | Kemp, Jr. et al. |
| 6,398,861 B1 | 6/2002 | Knox |
| 7,151,153 B2 | 12/2006 | Bruchmann et al. |
| 7,205,351 B2 | 4/2007 | Pritschins et al. |
| 7,485,365 B2 | 2/2009 | Schuster et al. |
| 7,511,085 B2 | 3/2009 | Bruchmann et al. |
| 2002/0050186 A1 | 5/2002 | Hanawa et al. |
| 2006/0118663 A1* | 6/2006 | Herzing ........................... 241/5 |
| 2007/0022901 A1 | 2/2007 | Kurze et al. |
| 2007/0199478 A1 | 8/2007 | Schlegl et al. |
| 2010/0047199 A1 | 2/2010 | Trummer et al. |
| 2010/0163420 A1 | 7/2010 | Weiss et al. |

FOREIGN PATENT DOCUMENTS

| CA | 843703 A | 6/1970 |
| DE | 202004005921 U1 | 4/2004 |
| DE | 10315775 A1 | 10/2004 |
| DE | 102006051893 A1 | 5/2008 |
| EP | 1304210 A1 | 4/2003 |
| EP | 1553144 A | 7/2005 |
| EP | 1529084 B1 | 6/2006 |
| GB | 1264584 A | 2/1972 |
| JP | 63000406 A | 1/1988 |
| JP | 2002327201 A | 11/2002 |
| WO | WO 02/36695 | 5/2002 |
| WO | WO 02/36697 | 5/2002 |
| WO | WO 2004/026972 A | 4/2004 |
| WO | WO 2006/066825 A | 6/2006 |
| WO | WO 2008/077612 A2 | 7/2008 |
| WO | WO 2009/144005 | 12/2009 |

OTHER PUBLICATIONS

International Search Report dated Feb. 26, 2010, issued in corresponding international application No. PCT/EP2009/003793.
European Search Report dated Oct. 22, 2008, issued in corresponding priority European application No. EP 08009699.3.
European Examination Report dated Mar. 2, 2010, issued in corresponding priority European application No. EP 08009699.3.

\* cited by examiner

*Primary Examiner* — Anthony J Green
(74) *Attorney, Agent, or Firm* — Ostrolenk Faber LLP

(57) ABSTRACT

Platelet-shaped, copper-containing, metallic effect pigments which have a copper content of 60% to 100% by weight, based on the total metal content, the metal pigments having a thickness distribution as determined via thickness counting by scanning electron microscopy (SEM) and represented as cumulative undersize distribution,
a) with an $h_{50}$ of 10 to 50 nm, and
b) with an $h_{90}$ of 20 to 70 nm,
the platelet-shaped, copper-containing, metallic effect pigments being produced by milling a copper-containing metal powder with lubricant. The disclosure further relates to a process for producing these pigments, and also to their use, to a printing ink comprising the pigments of the invention, and to a coated article comprising these pigments.

19 Claims, 1 Drawing Sheet

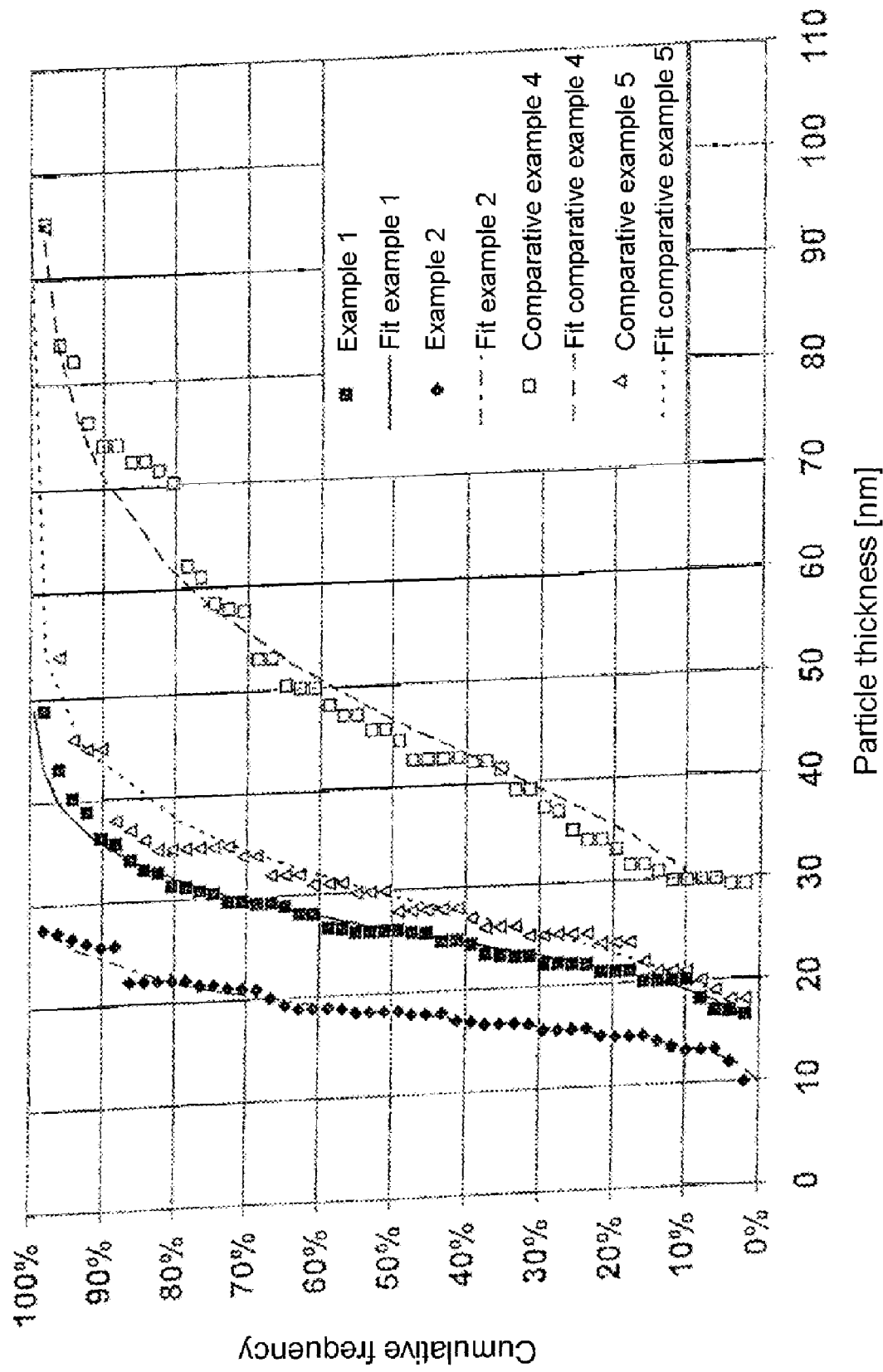

PLATELET-SHAPED, COPPER-CONTAINING, METALLIC EFFECT PIGMENTS, PROCESS FOR PREPARING THEM AND USE THEREOF

CROSS REFERENCE TO RELATED APPLICATIONS

The present application is a 35 U.S.C. §371 National Phase conversion of PCT/EP2009/003793, filed May 28, 2009, which claims benefit of European Application No. 08009699.3, filed May 28, 2008, the disclosure of which is incorporated herein by reference. The PCT International Application was published in the German language.

TECHNICAL FIELD

The invention relates to platelet-shaped, copper-containing, metallic effect pigments, to their preparation and use, and also to a coating composition comprising said pigments and to an article coated with said pigments.

BACKGROUND

Copper-containing, metallic effect pigments comprising copper pigments or brass pigments produced from a copper-zinc alloy, and also referred to as gold bronze pigments, are used in industries including the graphics industry among others, such as in printing inks, for example.

The metallic effect pigments produced from copper or brass powder by milling (conventionally predominantly in a dry milling operation) and used today for the pigmentation of flexographic and gravure inks, such as, for example, "Rotovario" gold bronze pigment dispersions or "Rotoflex" stabilized leafing gold bronze pigment powder or "Rotosafe" stabilized leafing gold bronze pigment pellets from Eckart GmbH, D-90763 Fürth, Germany, have leafing properties which impose conditions on their suitability for the pigmenting of film reverse applications with mirrorlike effect.

The use of brass pigments produced by PVD methods in printing inks is also problematic in that homogeneous metallization of the two metals (copper and zinc) for the purpose of achieving a uniform hue is extremely difficult technically to accomplish, with very different vaporization temperatures, in a high vacuum. Moreover, the PVD brass pigments, which are relatively expensive to produce, differ from brass pigments produced by conventional milling in having not very compact layers, with densities below the densities of the respective materials, and the desired gold hues (especially rich gold) cannot be realized at the low film thicknesses desired.

EP 1 529 084 B1 describes gold bronze pigments which can be produced by PVD methods. On account of the complex method, these pigments are very expensive. Moreover, these pigments have a propensity toward partial phase separation of the alloy constituents, a phenomenon likewise accompanied by unwanted shifts in hue and inadequate hue stabilities.

In addition, no copper-containing effect pigments produced by PVD methods have been available commercially to date.

The PVD aluminum pigments that are therefore normally used for the pigmentation of film reverse applications with mirrorlike effect, such as the "Metalure" products from Eckart GmbH, for example, do feature a homogeneous surface nature with a perfect nonleafing behavior, but have to be color-tinted with yellowish toner pigments. Printing inks of this kind trade under the product name "Ultrastar" from Eckart, for example, as solventborne gravure and flexographic inks. On account of the complex mode of production, PVD metallic effect pigments are generally much more expensive than metallic effect pigments produced by means of milling, conventionally.

In reverse application, as it is called, where a transparent film is printed with the printing ink, these printing inks can be used to produce a virtually perfect metal mirror. The mirror, however, is visible only if the application is viewed from the film side. Because of the admixed yellowish toner, the metal mirror appears in golden hues. The silver luster of the aluminum pigments, accordingly, mixes with the inherent color of the colorants.

A disadvantage of these printing inks is that their color is not very intense. The PVD aluminum pigments tend to accumulate in the vicinity of the film, i.e., in the lower region of the printed film. Because of this, however, there is little color pigment present between aluminum pigments and film, and this lessens the color strength.

If the concentration of color pigment is increased for compensation, corresponding luster losses are the inevitable consequence.

The printing ink, furthermore, has disadvantages when applied to absorbent substrates such as paper, for example, on account of the possibility for separation between metallic pigment and color pigment.

In order to produce conventional brass pigments produced from brass powder by milling, high-purity, electrolytically obtained copper and zinc are used as starting material for the milling operation, and are alloyed with addition of a little aluminum as reducing agent. For this purpose, copper and zinc are melted with one another, and the brass melt produced is atomized to form a coarse, nodular brass powder. The brass powder obtained is then ground into brass flakes. The milling of brass powder is carried out predominantly by the Hametag dry milling process. In this process, the coarse brass powder is ground in ball mills in a number of milling stages under different milling conditions, such as mill size, mill diameter, rotational mill velocity, ball size, and milling time, for example, with addition of lubricant, such as stearic or oleic acid, for example, in order to prevent cold welding of the copper or brass particles, and with grinding assistants, such as steel balls, for example.

For the dry milling of brass powder, the coarse, nodular brass powder used as milling product is ground to form platelet-shaped brass pigments. The density of the brass platelets, which are relatively difficult to deform, is around three times as high as that of comparable aluminum platelets. Following milling and classifying, the brass pigments are collected in different containers and then homogenized. In order to give the subsequent, metallically pigmented coatings the requisite metallic luster, it is possible, during the subsequent aftertreatment, for additional additives (such as stearic acid, for example) to be "polished on" to the surface of the pigment platelets.

In the case of brass pigments (gold bronze pigments), the hue of the alloy is determined by the ratio of copper to zinc. Generally speaking, the copper content is between 70% and 100% by weight. Gold bronze pigments trade, in characteristic natural hues, as "pale gold" with a copper fraction of around 90% by weight, remainder zinc; as "rich pale gold" with a copper fraction of around 85% by weight, remainder zinc; and as "rich gold" with a copper fraction of around 70% by weight, remainder zinc.

The production of platelet-shaped brass pigments by milling of brass powder in the presence of grinding auxiliaries is known to a person skilled in the art of pigment production, and is described in DE 2007717 A, for example. In this process for producing brass pigments, using a wet milling operation carried out with an inert liquid, the ground product is separated into at least three particle size fractions, i.e., into two coarse fractions and one fine fraction having a particle size of less than 44 μm. The fine fraction produced is recovered, and the middle coarse fraction is removed from the operation, while at least one coarse fraction is recycled with the oversize to the mill (ball mill).

JP 63000406A shows a process for the simple and cost-effective production of metal powder. The powder particles consist of metal flakes produced by mechanical milling, in ball mills, for example, using oil and water, including, for example, flakes of brass, having a high form factor and a normal pigment diameter and thickness.

JP 2002327201A relates to a golden powder for dip coating, composed of brass flakes having an average pigment diameter of 40-60 μm, a bulk density of 0.5-0.7 g/cm$^3$, and a covering area of at least 7000 cm$^2$/g.

U.S. Pat. No. 2,002,891A relates to the production of a bronze powder from aluminum, copper or other metals and their alloys. The metal used is milled under defined milling conditions to form flake-, platelet- or scale-shaped powder particles.

U.S. Pat. No. 3,995,815 A describes a process for producing metal powder comprising flakes, by means of a wet milling operation, defined by mixing ratios and milling times, and carried out on metals in ball mills. No details of the milled products are given by this publication.

U.S. Pat. No. 4,172,720 A discloses a flake-shaped metal powder with narrow thickness distribution, pure color, and a very high mirror effect. This known metal powder is produced from metal, including, for example, from brass, by a wet milling operation characterized by particular weight ratios of grinding assistant, metal, lubricant, and milling liquid.

Copper flakes with a thickness of below 3 μm and a diameter below 10 μm can be produced by the process described in U.S. Pat. No. 4,884,754. In that process, copper particles are milled in a nonpolar organic solvent, in the presence of one or more organic lubricants.

Subsequently the main fraction of organic lubricant and solvent is removed, and the copper flakes obtained are milled again, in a jet mill.

Copper flakes having a diameter of 4 to 10 μm and a form factor of 2 to 20 for application in electrically conductive pastes, for example, are described in US 2002/0050186 A1.

Thin, platelet-shaped aluminum pigments with a narrow thickness distribution are known from WO 2008/077612 A2. These aluminum pigments have a thickness $h_{50}$, determined via thickness counting by scanning electron microscopy, of 15 to 75 nm.

The high market demands that exists for printing inks, especially for gravure and flexographic inks for producing gold-colored mirrorlike effects cannot at present be satisfied.

SUMMARY

It is an object of the present invention to provide platelet-shaped, copper- to gold-colored metallic effect pigments having improved optical properties such as higher gloss and improved opacity. With printing inks, especially with gravure inks and flexographic inks, the metallic effect pigments are to have improved optical properties in combination with an improved split resistance.

A further object was to provide plated-shaped, copper- to gold-colored metallic effect pigments, producible in a simple and cost-effective way, for use for film reverse applications with mirrorlike effect.

The object is achieved through the provision of platelet-shaped, copper-containing, metallic effect pigments which have a copper content of 60% to 100% by weight, based on the total metal content, and have a thickness distribution as determined via thickness counting by scanning electron microscopy (SEM) and represented as cumulative undersize distribution, a) with an $h_{50}$ of 10 to 50 nm,
b) with an $h_{90}$ of 20 to 70 nm, the platelet-shaped, copper-containing, metallic effect pigments being produced by milling a copper-containing metal powder with lubricant.

Preferred developments of the metallic effect pigments of the invention are described further herein.

The object on which the invention is based is further achieved by a process for producing platelet-shaped, copper-containing metallic effect pigments which comprises the following step:

milling a copper-containing metal powder having a particle size distribution with a $d_{powder,50}$ of 1 to 15 μm and a $d_{powder,90}$ of 2 to 27 μm and a copper content of 60% to 100% by weight, based on the total metal powder, to form platelet-shaped, metallic effect pigments, using a milling apparatus, in the presence of lubricants and grinding media and optionally solvent, the resultant platelet-shaped metallic effect pigments having an average thickness as determined by thickness counting by scanning electron microscopy (SEM) with an $h_{50}$ of 10 to 50 nm and an $h_{90}$ of 20 to 70 nm.

Preferred developments of the process are specified further herein.

The object of the invention is further achieved through the use of the pigments of the invention as described herein and also through a printing ink as also described herein, comprising the copper-containing, metallic effect pigments of the invention, as well as an article as described herein, coated with the metallic effect pigments of the invention.

BRIEF DESCRIPTION OF THE FIGURE

FIG. 1 illustrates the thickness distribution of pigments used in samples according to the present invention as well as in several comparative examples.

DETAILED DESCRIPTION

Platelet-shaped, copper-containing, metallic effect pigments of the invention are understood in the context of the invention to be metallic effect pigments comprising or consisting of copper or of an alloy including or composed of zinc and copper (brass), having a copper content of at least 60% by weight, based on the total metal content of the pigments.

The copper-containing metallic effect pigments of the invention encompass copper pigments and also brass pigments (gold bronzes).

The copper effect pigments possess a copper content of 98% to 100% by weight, and preferably of 99% to 99.999% by weight. It is self-evident that a person skilled in the art reads the indication "100% by weight" of copper to include a very small fraction of any foreign metals that may be present.

The brass pigments, typically referred to as "gold bronzes", preferably have a copper content of 70% to around 90% by weight. The zinc content, correspondingly, is between 30% and 10% by weight, and here there may likewise be up to 2% by weight, preferably below 1% by weight, of other metals present as impurities.

Another preferred embodiment, indeed, deliberately uses an "impurity" with, for example, 0.5% to 2% by weight aluminum content, based on the total metallic effect pigments. Alloys of this kind have proven to be more stable to corrosion.

On account of their very low average thickness, the platelet-shaped, copper-containing, metallic effect pigments of the invention with nonleafing properties possess a very high opacity. The opacity of a pigment is the usual term for the coverage of a surface area per unit weight of pigment amount. The less the average thickness of the pigments, the greater the area covered by the pigment, and hence the greater its opacity.

Very thin metallic effect pigments having a very narrow thickness distribution are stacked more uniformly in the application medium than are metallic effect pigments having a broad thickness distribution. With the conventional metallic effect pigments, disuniformities in the stacking of the pigments in the application medium may readily occur. For instance, very thick metallic effect pigments in particular may act as "spacers", and this impairs the orientation of the surrounding or adjacent pigments in the application medium. This in turn has an adverse influence on gloss, on flop, and, under certain circumstances, on the opacity of the metallic effect pigments. It is especially deleterious in its effect in printing applications. In comparison to coatings, prints have a substantially lower film thickness and a lower binder fraction.

Determining the exact average thickness of platelet-shaped metal pigments is difficult. In practise, pigment thickness is determined by way of the degree of water coverage (spreading in accordance with DIN 55923) or by scanning electron microscopy (SEM). The degree of water coverage allows calculation only of an average thickness h for the pigments, but not of the thickness distribution. In order to determine the thickness distribution as well, the average thickness of the pigments of the invention has been determined for the purposes of this invention by means of scanning electron microscopy (SEM). With this method, a sufficient quantity of particles is measured that a representative statistical evaluation can be made. Typically, about 50 to 100 particles are measured.

The thickness distribution is usefully represented in the form of a cumulative undersize curve or cumulative frequency distribution. An appropriate average value is the $h_{50}$ of the cumulative undersize thickness curve. A measure of the coarse fraction is the $h_{90}$ value. The $h_{90}$ expresses the possession, by 90% of all of the pigment particles, of a thickness equal to this figure, and/or below this figure. Correspondingly, for example, an $h_{98}$ value expresses the possession by 98% of all of the pigment particles of a thickness equal to this figure and/or below this figure. Similarly, the $h_{10}$ is a measure of the fine fraction of the thickness distribution, and expresses the possession by 10% of all of the pigment particles of a thickness equal to this figure and/or below this figure.

The term "cumulative undersize distribution" used in accordance with the invention is also referred to as "cumulative frequency distribution". These two terms can therefore be used interchangeably, and hence in the present specification the term "cumulative frequency distribution" may also be used instead of the term "cumulative undersize distribution".

These characteristic values referred to above may be determined arithmetically from a list of the individual values measured, by means, for example, of the "quantile" function in an Excel representation. Determining the thicknesses of the individual pigments by means of SEM takes place in accordance with the method described in DE 103 15 775 A1.

In the result of the thickness count by scanning electron microscopy ($h_{50}$ of the cumulative undersize distribution or cumulative frequency distribution), an average thickness $h_{50}$ for the gold bronze pigments of the invention of 10 to 50 nm, preferably of 15 to 45 nm, more preferably of 15 to 40 nm, and very preferably of 20 to 35 nm, was ascertained.

Below an average thickness $h_{50}$ of 10 nm, the resulting hues of the metallic effect pigments become too dark, which is attributable to a reduction in reflection capacity with retention of the high absorption properties of the copper or brass. Likewise, owing to the increasing transparency of the metallic effect pigments, there is a reduction in the opacity, and unwanted shifts in hue may come about.

Above an average thickness $h_{50}$ of 50 nm, advantageous optical properties were present only in a greatly attenuated form for the metallic effect pigments of the invention.

Furthermore, the metallic effect pigments of the invention have a thickness distribution, as determined via thickness counting by scanning electron microscopy (SEM), with an $h_{90}$ of 20 to 70 nm, preferably of 20 to 60 nm, more preferably of 21 to 50 nm, and very preferably of 22 to 40 nm.

Above an $h_{90}$ of 70 nm, the advantageous properties of the metallic effect pigments of the invention were no longer observed. In particular it was no longer possible to ascertain a clear mirror in the film reverse application (with very good distinctness of image).

Platelet-shaped, copper-containing, metallic effect pigments having an $h_{90}$ of below 20 nm were not hitherto producible by milling.

It is thought that the advantageous optical properties of the metallic effect pigments of the invention derive from the very low thickness of all of the pigments in the pigment thickness distribution. The $h_{98}$ ought therefore to be preferably in the range from 21 to below 80 nm, more preferably from 24 to 70 nm, and very preferably from 25 to 60 nm.

The low thicknesses of the copper-containing, metallic effect pigments of the invention advantageously result in very good orientation of the pigments in the application medium, as for example in a printing ink, more particularly in a gravure ink and flexographic ink, for producing gold-colored film reverse applications. It is thought that, above a particular platelet thickness, these platelets are so flexible that they conform perfectly to the substrate. This effect is well established for PVD aluminum pigments, and is exploited particularly in film reverse applications.

In one further-preferred embodiment of the invention, the metallic effect pigments of the invention have an $h_{10}$ of the thickness distribution in the range from 8 to 25 nm and more preferably from 10 to 20 nm. Below an $h_{10}$ of 8 nm, the pigments are too thin, and this leads to impaired optical properties. Above an $h_{10}$ of 25 nm, in turn, the pigments are too thick, since with high $h_{10}$ values the $h_{50}$ and $h_{90}$ figures, correspondingly, are larger.

Moreover, the metallic effect pigments of the invention have a relative breadth of the thickness distribution $\Delta h$, as determined via thickness counting by scanning electron microscopy (SEM), which is calculated from the corresponding cumulative undersize curve of the relative frequency according to the formula $$\Delta h = 100 \times (h_{90} - h_{10})/h_{50},$$

of 30% to 90%, preferably of 35% to 85%, and more preferably of 40% to 80%.

On account of the narrow thickness distribution of the metallic effect pigments of the invention produced by wet milling, this narrow thickness distribution being similar, surprisingly, to that of PVD metallic effect pigments, the pigments of the invention are similar in terms of their optical properties to PVD pigments, but can be produced substantially more cost-effectively.

In longitudinal extent, the metallic effect pigments of the invention, produced in particular by wet milling of copper or brass powder, are basically no different from commercially traded gold bronze pigments produced by dry milling of copper or brass powder. On an individual basis, the pigment sizes are dependent on the intended use.

The copper-containing, metallic effect pigments of the invention preferably have an average size $d_{50}$ of 3 to 50 µm, more preferably of 4 to 30 µm, very preferably of 5 to 20 µm, and especially preferably of 6 to 15 µm. The longitudinal extent d (diameter) is determined in laser diffraction experiments on the basis of the Fraunhofer diffraction and/or Mie scattering theory. The evaluation of the diffraction data is based on a model which is geared to the diameter of an equivalent sphere. For this reason, the values obtained are not absolute, but the diameters measured have become established as reliable relative values in the description of the size characteristics of platelet-shaped metal pigments.

The $d_{50}$ value of the pigment length corresponds to 50% of the cumulative undersize distribution curve, measured and evaluated in the form of a volume distribution of equivalent spheres.

Entirely surprisingly it has been found that the coating compositions pigmented with copper-containing, metallic effect pigments of the invention, in "film reverse applications", exhibit a gold-colored mirrorlike effect which it was hitherto not possible to realize with conventional copper-containing metallic effect pigments produced by dry milling.

By a "film reverse application" is meant that a printing ink pigmented with metallic effect pigments is printed onto a transparent film. The print cured on the film, when copper-containing, metallic effect pigments of the invention are used, produces a golden (gold-colored) mirrorlike effect when viewed from the reverse. This mirror effect comes about as a result of the fact that the copper-containing, metallic effect pigments of the invention, because of their low thickness and their narrow thickness distribution, and also because of their nonleafing properties, are oriented directly at the film surface.

As a driving force for a plane-parallel orientation of metallic effect pigments, in addition to the interface-chemical incompatibility of the pigments with the binder system, the form factor is another important characteristic for the properties of the metallic effect pigments of the invention.

The form factor f is understood to be the ratio of the average longitudinal extent to the average thickness of the pigment platelets.

The dimensionless form factor f in this invention is defined as:

$$f = 1000 * \frac{d_{50} \ (\mu m)}{h_{50} \ (nm)}$$

The copper-containing, metallic effect pigments of the invention (gold bronze pigments) preferably have a form factor f of 150 to 3000. The pigments of the invention are characterized preferably by a form factor f of 250 to 2500, more preferably of 300 to 1000, and very preferably of 325 to 600.

In the case of prints, the binder fractions and the film thicknesses are generally very much lower than in coatings. This is especially true of gravure inks. Gravure inks pigmented with commercially traded gold bronze pigments have a solids content of approximately 40% by weight. Printed films of such inks have a wet film thickness of around 3 to 6 µm and a dry film thickness of around 1.5 to 3 µm. In the case of gravure inks pigmented with PVD pigments, the solids fractions are around 5% to 20% by weight of the total gravure ink. The associated dry film thicknesses are therefore only 0.5 to 1.5 µm. At these extremely low film thicknesses, largely uniform plane-parallel orientation of the metal pigments is necessary. This has been hitherto achievable only with PVD metallic effect pigments.

Print applications pigmented with the copper-containing, metallic effect pigments of the invention, especially film reverse applications, have optical effects (in respect of luster/mirror), on account of the low average particle thickness and the narrow particle thickness distribution of the pigments of the invention, that are comparable with those of print applications pigmented with conventional PVD metallic effect pigments.

In another preferred embodiment of the invention, the surface of the metallic effect pigments of the invention is covered at least partly with an additive, the additive comprising, as structural units, at least one carboxylic acid having at least four carbon atoms, and at least one polyglycol ether, the carboxylic acid and polyglycol ether being bonded covalently to one another.

By "structural units" is meant in accordance with the invention that the additive comprises a carboxylic acid having at least 4 carbon atoms. The carboxylic acid may be present as such or as a substituent, in the form of a side chain, for example. It is essential that the additive used in any case has at least one structural unit in the form of a carboxylic acid having at least 4 carbon atoms.

Additives of this type have proven, surprisingly, to be outstanding lubricants for the milling of copper-containing metal powder to form metallic effect pigments.

In the additive, the polyglycol ether is preferably esterified with the at least one carboxylic acid.

According to another preferred embodiment, carboxylic acids used are dicarboxylic acids, tricarboxylic acids, tetracarboxylic acids or mixtures thereof. As dicarboxylic and/or tricarboxylic acids that can be covalently bonded to polyglycol ether, it is likewise possible to use saturated and/or unsaturated carboxylic acids.

Examples of dicarboxylic acids which can be used include succinic acid, glutaric acid, adipic acid, pimelic acid, suberic acid, azelaic acid and/or sebacic acid.

In accordance with one preferred development of the invention, dicarboxylic, tricarboxylic or tetracarboxylic acids with relatively long carbon frameworks are used, as for example with 11 to 30 carbon atoms, preferably with 12 to 24 carbon atoms, more preferably with 14 to 22 carbon atoms. These dicarboxylic, tricarboxylic or tetracarboxylic acids are formed preferably by di-, tri- or tetramerization of unsaturated fatty acids such as, for example, oleic acid, linoleic acid, linolenic acid, eleostearic acid or similar acids.

Dicarboxylic acids having a carbon backbone of 18 carbon atoms have proven very suitable. This dicarboxylic acid, accordingly has 36 C atoms, and the corresponding tricarboxylic acid has 54 C atoms. It is preferred to use mixtures of these different fatty acids.

With regard to the polyether structural unit of the additive, in accordance with one preferred development of the invention, the polyglycol ether comprises the group $R^1$—O—$(R^2$—O$)_y$—$(R^3$—O$)_z$—$(R^4$—O$)_k$—, where the $R^2$—O, $R^3$—O, and $R^4$—O polyether units may be arranged randomly, alternatingly or as block copolymers. In this group, $R^1$ is a linear or branched aliphatic radical or araliphatic or aromatic organic radical having 1 to 30 carbon atoms. The radicals $R^2$, $R^3$ and $R^4$ may be identical or, independently of one another, different and are in each case a linear or branched aliphatic organic radical or araliphatic or aromatic organic radical having 1 to 12 carbon atoms. The individual degrees of polymerization y, z, and k are, independently of one another, 0 to 200, with the proviso that the total degree of polymerization y+z+k=2 to 600.

The radical $R^1$ is preferably a linear or branched aliphatic radical or araliphatic or aromatic organic radical having 2 to 16 carbon atoms, and more preferably an aliphatic radical having 1 to 12 C atoms.

The radicals $R^2$, $R^3$, and $R^4$ preferably, independently of one another, have 2 to 8 C atoms, and more preferably 2 to 4 C atoms.

With particular preference the radicals $R^2$, $R^3$, and $R^4$ independently of one another are ethyl, isopropyl, -propyl or butyl. Particular preference is additionally given to alternating ethyl and isopropyl units, referred to as EO/PO polyethers.

The length of the ether units (total degree of polymerization) y+z+k is preferably 5 to 300, more preferably 7 to 100, and very preferably 10 to 50.

Corresponding compounds are found for example in EP 1 304 210 A1. There, however, the compounds are described only as process agents for plastics, and not as lubricants for the production of metallic effect pigments.

Furthermore, the metallic effect pigments of the invention may have a metal oxide layer, the metal of the metal oxide layer being of the same type as the metal of the metallic effect pigment.

Oxide layers of this kind are also known from the typical copper and gold bronze pigments. These oxide layers are obtained by oxidation. On account of their inherent colors and of interference effects, these metal oxide layers, depending on their layer thickness, produce effect pigments with a wide variety of different hues in the yellow-red color range. It will be appreciated that the base color of the metal pigment also has a large part to play here.

Since, of course, the oxidation always converts only part of the metal into the corresponding oxide, it is preferred not to employ the thinnest metal pigments of the invention for oxidation. Such pigments would have only a very small remaining metal content, or none at all, and that would have great disadvantages in relation to their opacity. For oxidation, therefore, only metal pigments of the invention having average thickness $h_{50}$ in the range from 25 to 50 nm are used.

The invention therefore further relates to oxidized, copper-containing, metallic effect pigments.

For use in water-containing media, as for example in aqueous printing inks or in weathering-resistant outdoor applications, the metallic effect pigments of the invention may be coated with a passivating inhibitor layer and/or passivating anticorrosion layer.

The mechanism of action of the inhibitor layers and/or passivating layers is complex.

In the case of inhibitors, the inhibiting or passivating effect is usually based on steric effects. The major part of the inhibitors, therefore, also have an orienting effect in the sense of leafing and nonleafing, i.e., floating or not floating in the application medium.

The inhibitors are added typically at low concentrations, in the order of 1% to 15% by weight, based on the weight of the metallic effect pigment used.

Passivating inhibitors that may find use for the metallic effect pigments of the invention include fatty acids, carboxylic acid derivatives, organic phosphates and phosphonates and their esters, organic-functionalized silanes, aliphatic or cyclic amines, aliphatic and aromatic nitro compounds, oxygen-, sulfur- or nitrogen-containing heterocycles, sulfur/nitrogen compounds of higher ketones, aldehydes, and alcohols, thiols, β-diketones, β-keto esters or mixtures thereof.

Contemplated for inhibiting the metallic effect pigments of the invention are, preferably, the following:

Organically modified phosphonic acids and/or their esters of the general formula R—P(O)(OR$_1$)(OR$_2$), where: R=alkyl, aryl, alkylaryl, arylalkyl, and also alkyl ethers, especially ethoxylated alkyl ethers, and $R_1$, $R_2$=H, $C_nH_{2n+1}$, with n=1-6, it being possible for alkyl in each case to be branched or unbranched. $R_1$ may be identical to or different from $R_2$.

Organically modified phosphoric acids and esters of the general formula R—O—P(OR$_1$)(OR$_2$) where R=alkyl, aryl, alkylaryl, arylalkyl, and also alkyl ethers, especially ethoxylated alkyl ethers, and $R_1$, $R_2$=H, $C_nH_{2n+1}$, with n=1-6, it being possible for alkyl in each case to be branched or unbranched. $R_1$ may be identical to or different from $R_2$.

Use may be made of pure phosphonic acids or esters, or phosphoric acids or esters, or any desired mixtures thereof.

Where the metallic effect pigments of the invention are milled in a predominantly aqueous solvent, inhibitors of this kind are used as grinding assistants, in order to prevent hydrogen being formed—which is hazardous from a safety standpoint—during the milling operation.

The passivating inhibitor layer may additionally comprise or be composed of corrosion-inhibiting, organically functionalized silanes, aliphatic or cyclic amines, aliphatic or aromatic nitro compounds, or oxygen-, sulfur- and/or nitrogen-containing heterocycles. Of these, nitrogen-containing heterocyclic compounds are preferred, with triazoles being particularly preferred and benzotriazoles especially preferred. Use may further be made, for example, of thiourea derivatives, sulfur compounds and/or nitrogen compounds of higher ketones, aldehydes and alcohols (fatty alcohols) or thiols, or mixtures thereof. The passivating inhibitor layer may alternatively be composed of the substances identified above. Preference is given to organic phosphonic acids and/or phosphoric esters or mixtures thereof. Where amine compounds are used, they preferably have organic radicals with more than 6 C atoms. It is preferred to use such amines together with organic phosphonic acids and/or phosphoric esters or mixtures thereof.

There are a variety of possible way of passivating metallic effect pigments by corrosion protection barriers with chemical and physical protective effect.

Passivating anticorrosion layers which ensure particularly good protection from corrosion for the metallic effect pigments of the invention comprise or are composed of silicon oxide, preferably silicon dioxide, zirconium oxide, cerium oxide, aluminum oxide, polymerized polymeric resins, phosphates, phosphites, borates or mixtures thereof.

Preference is given to silicon dioxide layers, the silicon dioxide surface preferably being coated with silanes.

The $SiO_2$ layers are produced preferably by sol-gel methods, with average layer thicknesses of 2 to 150 nm and preferably of 5 to 40 nm, in organic solvents.

The copper-containing, metallic effect pigments of the invention are used preferably in the form of pigment paste, more preferably in the form of a pastelike product for gravure and flexographic printing inks.

The process for producing the plated-shaped, copper-containing, metallic effect pigments of the invention is set out below.

The copper-containing, metallic effect pigments of the invention are produced by milling a copper-containing metal powder with lubricant. This milling operation is preferably a wet milling. The copper-containing metal powder is preferably a copper or brass powder.

More preferably the milling operation is one which comprises a gentle step of deformative milling of copper or brass powder. With further preference, the copper or brass powder has a very narrow particle size distribution.

A process for producing platelet-shaped, copper-containing, metallic effect pigments comprises the following step:
milling of a copper-containing metal powder having a particle size distribution with a $d_{powder,50}$ of 1 to 15 µm and a $d_{powder,90}$ of 2 to 27 µm and a copper content of 60% to 100% by weight, based on the total metal powder, to form platelet-shaped metallic effect pigments, using a milling mechanism, in the presence of lubricants and grinding media and optionally solvent,
the platelet-shaped metallic effect pigments having an average thickness, as determined by thickness counting by scanning electron microscopy (SEM), with an $h_{50}$ of 10 to 50 nm and an $h_{90}$ of 20 to 70 nm.

The milling is more preferably a wet milling operation in the presence of solvent.

In a further preferred embodiment of the invention, the powder particles are milled in two stages. In the first of these stages, the powder particles undergo preliminary deformation, and in the second stage they are milled to completion.

The preliminary deformation step here is carried out under conditions which allow a relatively high energy input onto the metal particles.

The two stages may be carried out, for example, with different ball sizes. In this case it is useful in the preliminary deformation step to select larger balls, which allow a higher energy input.

With this process, however, it is necessary to operate in two stages, which is relatively costly and inconvenient.

With further preference, therefore, the two stages are carried out in one mill with the same grinding media charge. In this case the different energy input can be brought about for example, by means of different rotational speeds of the mill and/or by means of different milling times.

In further-preferred embodiments, the copper-containing metal powder has a $d_{powder,50}$ of 1.5 to 10 µm and more preferably of 2 to 5 µm. It is further preferred for the copper-containing metal powder to have a $d_{powder,90}$ of 2.5 to 20 µm and more preferably of 3 to 7 µm.

Furthermore, the copper or brass powder used in accordance with the invention preferably has a span $\Delta d_{powder} = (d_{powder,90} - d_{powder,10})/d_{powder,50}$ of 0.8 to 1.7 and more preferably of 0.9 to 1.3.

This copper or brass powder is a very fine metal powder having a very narrow size distribution. The particle size distribution band is typically determined by laser diffraction spectrometry, the particle size being ascertainable from the diffraction of laser light. The laser diffraction spectrometry is carried out preferably with the Helos instrument from Sympatec GmbH, Clausthal-Zellerfeld, Germany, in accordance with manufacturer details.

The metal powder used for producing the copper-containing metallic effect pigments of the invention is produced preferably in atomizers by atomization of liquid copper or of a copper-zinc alloy, i.e., brass, preferably from a copper melt or brass melt. The powder obtained following atomization of a copper or brass melt is classified in accordance with one preferred variant, in order to give the desired particle size distribution, which may also be referred to as particle size band.

Following the atomizing step, the copper or brass powder can be brought to the desired narrow size distribution by means of corresponding classifying steps. Classifying can be carried out using air classifiers, cyclones, and other known devices.

The use of a fine copper or brass powder of this kind with narrow size distribution is of essential importance to the production of the platelet-shaped, copper-containing metallic effect pigments of the invention.

During the deformative milling, the copper or brass powder particles are not deformed in a completely uniform way: This means that certain metal particles are deformed more greatly, while some of the powder particles are only deformed at a very late stage during milling. Among the reasons for this is the fact that the deformation probability for a metal particle is dependent on its size. Thus, metal particles which have already undergone preliminary deformation to platelets possess a higher specific surface area than metal powder which has been yet deformed, and, accordingly, possess a higher probability of being deformed further. The breadth of the size distribution of the metal powder is therefore reflected not only in the size distribution of the copper or brass platelets formed from it, but also in the distribution of the thickness distribution. For narrow thickness distributions, therefore, it is necessary to use a copper or brass powder with a correspondingly low size variation.

The atomizing step can be carried out in an air atmosphere or under inert gas atmosphere. Inert gases used are preferably nitrogen and/or helium.

The purity of the copper or copper-zinc alloy (brass) used at the atomizing stage is preferably 99.0% to above 99.9% by weight. The powder may comprise, in correspondingly small amounts, the typical alloying constituents (e.g., Al, Si, Fe, Sn, Pb). It is preferred for 0.1%-2% by weight of aluminum to be alloyed in.

Wet milling of the copper or brass powder of the invention takes place in conventional mills, preferably in a ball mill, stirred ball mill, edge runner mill, drum ball mill or rotary tube ball mill, in the presence of solvent and lubricants as grinding assistants, and also using grinding media.

In the course of the wet milling, taking place in at least two steps, of the copper or brass powder of the invention, grinding media, preferably spherical grinding media, having an average diameter of 0.3 up to 4.7 mm and preferably of 0.6 to 2 mm are used.

The grinding media used in diverse embodiments, such as balls, ellipsoids, cylinders, cuboids, etc., for example, are preferably composed of chromium steel, steel, glass or ceramic. With particular preference the grinding media are composed of chromium steel. Furthermore, grinding media used with particular preference are preferably spherical media, more preferably balls.

Preference is given to spherical grinding media having a very smooth surface, a very round form, and uniform size.

The grinding media used for the wet milling of the copper or brass powder preferably have an individual weight of 85 µg to 425 mg.

In accordance with one preferred development of the invention, the grinding media have an individual weight of 0.8 to 180 mg.

In the case of steel balls, the average individual weight is preferably in a range from 1 to 180 mg, preferably from 1.2 to 150 mg, more preferably from 2.0 to 120 mg. In the case of glass balls, the average individual weight is in a range from 1.0 to 12.5 mg.

Owing to the extremely gentle mode of milling, the duration of this milling is comparatively long.

The milling time is preferably 10 to 100 hours, preferably 20 to 60 hours, and more preferably 30 to 50 hours.

These times are understood to be the total times of the milling duration.

If milling is carried out in two or more different steps, then the milling durations of the individual steps must be added up accordingly.

These long milling times result in a large number of pigment/grinding media impacts. As a result, the pigment is very uniformly shaped, resulting in a very smooth surface and a very narrow thickness distribution.

This cannot be achieved, generally, in a milling time of less than 10 hours. Milling times above 100 hours conversely, are more and more uneconomic.

The temperatures during the milling operation are situated in the range from 15° C. to 55° C. Preference is given to temperatures in a range from 20° C. to 35° C.

At the milling stage, copper or brass powder of defined particle size is introduced together with solvent, white spirit for example, into a ball mill.

Solvents used may be commercially customary, organic solvents, preferably white spirit, solvent naphtha, alcohols, glycols, esters, ethers, ketones or mixtures thereof.

Milling ought preferably to be carried out in solvents which are compatible with the subsequently planned application.

For example, for application in a gravure ink, solvents such as ethyl acetate, n-propyl acetate or isopropyl acetate are preferred.

The rewetting step which is typically practised with aluminum pigments is not advisable here. In the case of rewetting, if it proves necessary, the metallic effect pigments, after milling, are largely freed from their solvent, under reduced pressure and at elevated temperatures, and are then pasted up again with the solvent that is compatible (and desired by the customer) for the particular end application.

Because of the very high specific surface areas of the metallic effect pigments of the invention, the rewetting step may be accompanied by unwanted instances of agglomeration of the metal pigments. Milling ought preferably, therefore, to be carried out in solvents which are compatible with the subsequently planned application.

It is likewise possible to use water (at least predominantly) as solvent. In that case, however, the lubricants employed should have a significantly corrosion-inhibiting effect. Preference is given here to phosphonic acids and/or phosphoric esters, which may also carry ethoxylated side chains. Here as well it is advisable to add further corrosion inhibitors in the course of milling.

Milling is carried out preferably in a solvent, with a weight ratio of solvent to metal particle of preferably 1.5:1 to 5:1, and more preferably of 2:1 to 4:1.

In order to prevent cold welding of the powder particles, lubricant, examples being oleic acid, stearic acid or else inhibitors, is added in an amount which is dependent on the particular free specific surface area (BET) of the rolled-out copper or brass pigments. Generally speaking, 1% to 30% by weight and preferably 1.5%-10% by weight of lubricant is used, based on the weight of the copper or brass powder.

There are a large number of compounds that may be used as lubricants in the course of milling.

Here, mention may be made in particular of the fatty acids that have been used for a long time, having alkyl radicals of 10 to 24 C atoms. It is preferred to use oleic acid or mixtures of different unsaturated fatty acids or mixtures of unsaturated and saturated fatty acids that lead to nonleafing pigments. In contrast to leafing pigments, which float to the surface in the application medium, nonleafing pigments undergo orientation in an application medium, such as a paint or a printing ink, for example. Additionally, for example, long-chain amino compounds may be added to the fatty acids. The fatty acids may be animal or else vegetable in origin.

The lubricant ought to be added in an amount which is not too small, since otherwise, owing to the high degree of shaping of the copper or brass powder, the very large surface areas of the plateletlike copper or brass pigments produced will be inadequately satisfied by adsorbed lubricant. In this case there may be instances of cold welding. Typical amounts are therefore 1% to 30% by weight, preferably 2% to 15% by weight, of lubricant, based on the weight of the copper or brass powder used.

A particularly preferred lubricant used is an additive, the additive comprising, as structural units, at least one carboxylic acid having at least 4 carbon atoms, and at least one polyglycol ether, the carboxylic acid and the polyglycol ether being bonded covalently to one another.

In this case it is particularly preferred for the carboxylic acids or fatty acids to be at least partly esterified with a polyglycol ether.

Thus, for example, use may be made of the fatty acid polyglycol ester "P4100" from BYK-Chemie, Wesel, Germany, which is available commercially as a processing assistant for plastics.

The weight ratio of grinding balls to metal particles is preferably 10:1 to 60:1, more preferably from 25:1 to 50:1.

In relation to milling in a ball mill, the critical speed $n_{crit}$ is an important parameter, indicating the point in time at which the balls are forced to the mill wall by the centrifugal forces, and milling virtually no longer takes place:

$$n_{crit} = \sqrt{\frac{g}{2\Pi^2} \times \frac{1}{D}}$$

where D is the drum diameter and g is the gravitational constant.

The rotational speeds in the ball mill are preferably 20% to 95%, more preferably 50% to 90%, and very preferably 55% to 86% of the critical speed $n_{crit}$.

The rotational speeds must not be too high, so as to favor slow deformation of the metal particles. On the other hand, the copper or brass powder (gold bronze powder), in contrast, for instance, to atomized aluminum powder, requires a relatively high energy input and therefore higher rotational speeds, owing to the lower ductility of brass (or copper). In order to bring about slow deformation, it is also preferred to use lightweight grinding balls in the process of the invention.

In contrast to conventional milling processes, the copper or brass powder in the process of the invention is predominantly not ground or comminuted, but instead is deformed very gently over a relatively long time period.

The conditions recited above result in a very gentle milling, where the metal powder is slowly shaped and fractures on the part of the metal particles as a result of ball impact with high kinetic energy are avoided.

The milled material is isolated by filtration, and the filter cake obtained is milled in a further ball mill with ball-shaped grinding media, solvent, and grinding additive.

The milled material is separated from the grinding balls by rinsing with solvent, and is subsequently concentrated.

In a further, preferred process step, the metallic effect pigments obtained may be subjected to size classification. This classification ought to be carried out gently, in order not to destroy the thin metal pigments. The classifying operation may be, for example, a wet sieving, a decanting or else a separation by sedimentation (by means of gravity or centrifuging). In the case of wet sieving, it is usually the coarse fraction that is sieved out. Subsequently, the suspension is separated from excess solvent (by means of a filter press, centrifuge or filter, for example).

In a further preferred process step, the copper-containing metallic element pigments of the invention may be subjected to an oxidation. In this pigment treatment, atmospheric oxygen acts on the copper-containing metallic effect pigment for a defined time period at a defined temperature, forming a thin oxide layer on the metal platelet. Through interference reflection, interesting color shadings are produced. Oxidized copper-containing metallic effect pigments are traded in hues which include English green, lemon, ducat gold and fire red shades.

The copper-containing metallic effect pigments of the invention may be provided advantageously as pastelike products in all known hues. The solids content of the pastes comprising metallic effect pigments of the invention is 30% to 90% by weight, preferably 40% to 75% by weight, and more preferably 45% to 70% by weight, based on the paste.

The very thin, copper-containing metallic effect pigments produced by milling differ from gold bronze pigments obtainable by PVD processes, of the kind of pigments described in EP 1 529 084 B1, for example.

First, surprisingly, the copper-containing metallic effect pigments of the invention in the case of gold bronzes have a largely homogeneous composition with regard to their two alloy constituents, copper and zinc. With the pigments produced by PVD processes it has emerged that there is often phase separation of the two metals.

Another structural difference is that the surfaces of the copper-containing metallic effect pigments of the invention naturally have a greater micro-roughness than that of pigments produced by PVD processes. This increased micro-roughness can be attributed to the action of the grinding media on the pigments.

A further structural difference between PVD pigments and the pigments of the invention can be recognized in the edge region of the pigments.

PVD pigments are produced by vapor deposition onto a support material, with subsequent detachment and comminution. As a result of this, PVD pigments generally have straight fracture edges. Furthermore, there is no decrease in the thickness of the PVD pigment from the center of the pigment to the edge region.

With the copper-containing effect pigments of the invention there is generally a flattening of the pigment thickness to the edge region. Furthermore, in general, the edge region does not have straight edges, but instead an irregularly shaped edge.

The structural differences, attributable to the different production processes, between PVD pigments and the pigments of the invention are readily recognizable in SEM micrographs.

With particular advantage the metallic effect pigments of the invention are converted by drying into a powder form, preferably into a nondusting powder form, as for example into a stabilized metal powder. The dried powder may be processed further in a suitable homogenizer to give a nondusting metal powder, by addition of very small amounts of solvent (<10%). It is also possible first to dry the filter cake and then to paste it up again with a different solvent (rewetting).

The metallic effect pigments of the invention may also, however, surprisingly, be converted, by adding a suitable dispersion of an appropriate resin to the filter cake, into granules, pellets, briquettes, tablets or sausages. These supply forms possess the advantages that they are nondusting, are easy to meter, and have outstanding dispersibility.

Pelletizing may be carried out on a pelletizing plate in a conventional way. Tableting may take place in a tableting apparatus. The sausages may be produced by a compression molding process from pigment paste or pigment powder, or by extruding such paste or powder through an extruder and using a rotary knife arrangement to chop up the extruded paste strands. Granulating the copper-containing metallic effect pigments of the invention (especially gold bronze pigments) can be done, for example, by spray granulation.

The copper-containing metallic effect pigments of the invention can be provided very advantageously in granules or pellets with high pigment contents, of 90% by weight to 35% by weight, for example, preferably 70% by weight to 40% by weight, based in each case on the total weight of the granule or pellet.

On account of the high specific surface area of the pigments of the invention, it is preferable to use relatively large amounts of dispersing resin for their pelletization. Preference is given to using 2% go 50% by weight, more preferably 5% to 30% by weight, of resin, based on the total formulation of the pellets.

There are a large number of dispersing resins that can be used for pelletizing. Examples of such resins include both naturally occurring resins and synthetic resins. They comprise, for example, alkyd resins, carboxymethyl- and carboxyethylcellulose resins, cellulose acetate, cellulose acetate propionate (CAP), and cellulose acetate butyrate (CAB), cumarol-indene resins, epoxide esters, epoxide-melamine and epoxide-phenol condensates, ethyl- and methylcellulose, ethylhydroxyethylcellulose, hydroxyethylcellulose, hydroxypropylmethylcellulose, ketone resins and maleic acid resins, rosins, melamine resins, nitrocellulose resins, phenolic and modified phenolic resins, polyacrylamide, polycarbonate, polyamide, polyester, polyether, polyurethane, and vinyl resins.

Among these polymeric resins, the following deserve particular mention: acrylate copolymers and acrylic ester resins, polyacrylonitrile and acrylonitrile-copolymer resins, copolymers of butadiene and vinylidene chlorides, butadiene/styrene copolymers, methyl acrylate and methyl methacrylate copolymers, and also polybutene, polyisobutylene, polyvinyl acetate, polyvinyl alcohol, polyvinyl chloride, polyvinyl ether, polyvinylpyrrolidone, and polystyrene resins. Other copolymers include styrene/maleic anhydride and styrene/shellac resins, vinyl chloride/vinyl acetate resins, vinyl chloride/vinyl ether resins, and vinyl chloride/vinylidene chloride resins.

Further contemplated are naturally occurring resins such as gum arabic, gutta percha, casein, and gelatin.

Preference is given to aldehyde resins, such as the Laropal series from BASF AG, Ludwigshafen. Furthermore, waxes are contemplated as binder materials. Mention is made here, as examples, of natural waxes such as beeswax, candelilla wax, carnauba wax, montan wax, and also paraffin waxes. Synthetic waxes such as PE waxes, for example, are also contemplated.

The aforementioned preparations can be incorporated very well, for example, into paint systems or printing inks, without instances of unwanted agglomeration of the pigments.

The copper-containing metallic effect pigments of the invention, with the typical coloristics of copper or brass, can be used in coating compositions such as coatings, paints, varnishes, printing inks, powder coatings, plastics, securities printing and security printing, ceramics, and cosmetic formulations.

The copper or brass pigments of the invention can be used with particular advantage in printing inks for gravure, flexographic or screen printing. Particularly preferred is the use of these pigments in gravure, screen, and flexographic printing inks for producing film reverse applications with mirrorlike effect.

The invention further provides a coating composition, preferably a printing ink, more preferably a gravure, flexographic or screen printing ink, which comprises the copper-containing metallic effect pigments of the invention.

Printing inks comprise solvents or solvent mixtures. One of the purposes of the latter is to dissolve the binders, but another is to set important performance properties of these printing inks, such as the viscosity or the drying rate, for example. Solvents used for gravure and flexographic inks comprise, in particular, low-boiling solvents. The boiling point is generally not more than 140° C. Higher-boiling solvents are used only in relatively small amounts, to set the drying rate.

Examples of suitable solvents for liquid printing inks include ethanol, 1-propanol or 2-propanol, substituted alcohols, such as ethoxypropanol or methoxypropanol, for example, or esters, examples being ethyl acetate, isopropyl acetate, n-propyl acetate, and n-butyl acetate. It is of course also possible to use mixtures of different solvents. For example, a mixture may be of ethanol and esters such as ethyl acetate or n-propyl acetate.

For printing with gravure and flexographic inks it is generally advisable for the ester fraction of the total solvent not to exceed around 20% to 25% by weight. Solvents which can be used for liquid printing inks also include water or predominantly aqueous solvent mixtures. Depending on the nature of the printing ink, it is usual to use 10% to 80% by weight of solvent, relative to the sum of all of the constituents.

For printing inks of the invention, however, a range from 60% to 80% by weight of solvent proves particularly advantageous.

Radiation-curable printing inks generally do not comprise the aforementioned solvents, but instead comprise reactive diluents. Reactive diluents typically fulfill a dual function. On the one hand, they act to crosslink or cure the printing ink; on the other hand, however, they also serve, like conventional solvents (DE 20 2004 005 921 U1), to adjust the viscosity. Examples include butyl acrylate, 2-ethylhexyl acrylate, and also, in particular, polyfunctional acrylates such as 1,4-butanediol di(meth)acrylate, 1,6-hexanediol di(meth)acrylate or trimethylolpropane tri(meth)-acrylate.

As binders for the printing inks of the invention it is possible in principle to use the binders that are customary for liquid printing inks. Depending on the desired end application and the desired properties, the skilled person makes an appropriate selection. Examples of suitable binders include polyester, polyamides, PVC copolymers, aliphatic and aromatic ketone resins, melamine-urea resins, melamine-formaldehyde resins, maleates, rosin derivatives, polyvinyl butyrals, casein and casein derivatives, ethylcellulose, nitrocellulose, or aromatic and/or aliphatic polyurethanes. Use may also be made of polymers or copolymers of vinyl acetate, vinyl alcohol, acrylates, methacrylates, vinylpyrrolidone or vinyl acetals. Of particular advantage may be the use of hyperbranched polymers containing functional groups, examples being hyperbranched polyurethanes, polyureas or polyester amides, as disclosed by WO 02/36695 and WO 02/36697. It is of course also possible to use mixtures of different polymeric binders, subject to the proviso that the binders selected do not exhibit unwanted properties when in combination with one another. The amount of all of the binders is typically 2% to 40% by weight, relative to the sum of all of the constituents of the printing ink.

Particularly preferred binders include, for example, nitrocellulose, ethylcellulose, hydroxyethylcellulose, acrylates, polyvinyl butyrals, and also aliphatic and aromatic polyurethanes and polyureas, especially hyperbranched polyurethanes and polyureas, and mixtures thereof.

Binders contemplated for water-reducible printing inks include, in particular, copolymers based on (meth)acrylic acid and/or esters thereof with styrene. Binders of this kind are available commercially as solutions or dispersions for use in printing inks, under the name Zinpol® (Worlee), for example. Further examples include aromatic and aliphatic aqueous polyurethanes, polyesters, and aqueous polyamides.

Binders preferred for offset printing inks include, for example, rosins or modified rosins. Examples of modified rosins include rosins esterified partly or wholly with polyols such as glycerol or pentaerythritol, for example.

Radiation-curable printing inks comprise binders which comprise crosslinkable groups, such as olefinic groups, vinyl ether groups or epoxide groups, for example.

Here, the sum of the binders (including reactive diluents) is generally in a range from 30% to 90% by weight of all of the constituents of the printing ink.

The printing inks of the invention may further comprise one or more auxiliaries or additives. Examples of additives and auxiliaries are fillers such as calcium carbonate, aluminum oxide hydrate or aluminum silicate or magnesium silicate. Waxes increase the abrasion resistance and serve to increase the lubricity. Examples are, in particular, polyethylene waxes, oxidized polyethylene waxes, petroleum waxes or ceresin waxes. Fatty acid amides may be used to increase the surface smoothness. Plasticizers serve to increase the elasticity of the dried film. For radiation-curable printing inks, furthermore, at least one photoinitiator or photoinitiator system is used as an additive. Dispersing assistants may be used for dispersing the effect pigments. Fatty acids may be used to bring about floating of the effect pigments in the printed layer, so that the pigments are accumulated in/at the upper boundary surface of the printed layer. Advantageously improved metallic effects may be obtained by this means. Moreover, antisettling agents may be added as well. Such additions prevent the sedimentation of the effect pigments. Examples include silica, cellulose derivatives, or else waxes.

In order to formulate the particularly preferred low-viscosity gravure or flexographic printing inks, the addition of antisettling agents is usually advisable, though not absolutely necessary. The total amount of all additives and auxiliaries ought typically not to exceed 20% by weight, relative to the sum of all of the constituents of the printing ink, and is preferably 0.1% to 10% by weight.

The printing inks of the invention can be produced in a way which is known in principle, by intensively mixing or dispersing the constituents in customary apparatus, examples being dissolvers or stirring mechanisms. When using dissolvers, the skilled person will ensure that the energy input is not too high, so as to prevent damage to the metallic effect pigments of the invention. Conversely, the energy input must of course by high enough to allow proper dispersing of the pigments. If typical color pigments are used alongside the metallic effect pigments of the invention, it may be advisable to predisperse these color pigments in a portion or in the entirety of the solvent, the binder, and, where appropriate, the auxiliaries of the printing ink, and not to add the pigments of the invention until later. In this way, the additional pigments are dispersed to particularly good effect, without damage to the pigments from excessive dispersing. Instead of the pigments it is also possible to use predispersed pigment concentrates. Especially elegant in this context may also be the use of a commercial printing ink in small amounts, subject to the proviso that the added printing ink is compatible with the formula of the printing ink and does not impair its properties.

The invention further provides a coated article whose coating comprises the platelet-shaped, copper-containing, metallic effect pigments of the invention.

The coated article may be a commodity article, such as a printed product or a motor vehicle, for example, or else an article which may be used for other (commercial) purposes, made of paper, paper board, cardboard, plastic, film, metal, glass, stone or other known materials.

EXAMPLES

The examples set out below illustrate the invention, but without restricting it.

Example 1 a) Metal Powder Atomization

Brass pigments of the invention were produced by charging an induction furnace with 70% by weight of copper and 30% by weight of zinc, and melting this initial charge. The brass melt was then transferred to a channel-type induction furnace with forehearth. The brass melt present in liquid form at a temperature of about 1050° C. in the forehearth was atomized vertically downward by means of an atomizing nozzle mounted in the forehearth. The nozzle used for atomizing the brass melt was a close-coupled nozzle. The brass particles formed in the course of atomization solidify and cool while in flight. Atomization took place with supply of hot air at about 400° C. The hot gas used for atomizing was compressed, then heated in gas heaters, and subsequently introduced into the brass melt to be atomized. The brass particles were deposited by means of centrifugal force. The brass powder deposited had a $d_{50}$ of <60 µm. Gas/solids separation took place in a filter. Further separation of this brass powder took place by means of further classifying steps. The result was an ultrafine brass powder ("brass 70:30 rich gold"), produced with a $d_{powder,10}$ of 1.4 µm, a $d_{powder,50}$ of 2.4 µm, and a $d_{90}$ of 4.0 µm, and also a $d_{powder,98}$ of 6 µm.

b) Preparation of Milling Additive

Based on EP 1 304 210 A1

50 g of Pripol 1009 (hydrogenated C36 dimer acid from Unichema) and 89 mg of MPEG 750 (methoxypolyethylene glycol) were weighed out into a glass reaction vessel and heated to 80° C. with stirring under $N_2$ inert gas. Then 0.8 g of p-toluenesulfonic acid (catalyst) was added and the mixture was heated to 180° C. Water of reaction formed was separated off on a water separator. The acid number was used to monitor the progress of the reaction. The acid number was determined in accordance with DIN 53402. The reaction was halted after an acid number of about 24 mg KOH/g additive had been reached. This corresponds to a degree of esterification of around 67%. The average molecular weight of the resulting ester was around 1750 g/mol.

c) Milling

For the wet milling of the ultrafine brass powder produced in step a), 400 g of this metal powder were introduced into a mill (length: 32 cm, width: 19 cm) with 10 kg of chromium steel balls (diameter: 3 mm) and 900 g of isopropyl acetate, and also 30 g of milling additive according to example 1b, and milling took place at 80 rpm for 30 hours. The milled product was separated from the grinding balls by rinsing with solvent, and isolated by filtration. The filter cake was then introduced into a second mill. The brass paste introduced into this mill, with a quantity of 400 g, was milled using 10 kg of chromium steel balls (diameter: 1.3 mm) with a rotational speed of 60 rpm for 30 hours, with around 900 g of isopropyl acetate and about 25 g of milling additive according to example 1b. The brass pigment paste was then separated from the grinding balls by rinsing with solvent, and was thereafter concentrated to a solids content of 70% by weight.

Example 2

Same as example 1, but using N-propyl acetate rather than isopropyl acetate as solvent during milling.

Example 3 a) Copper Powder Atomization

Copper pigments of the invention were produced by charging an induction furnace with copper and melting this initial charge. The copper melt was then transferred to a channel-type induction furnace with forehearth. The copper melt present in the forehearth was atomized vertically downward by means of an atomizing nozzle. The copper particles formed in the course of atomization solidified and cooled while in flight. Atomization took place with supply of hot air at about 500° C. The copper particles were deposited by means of centrifugal force. The deposited copper powder had a $d_{powder,50}$ of <60 µm. Gas/solids separation took place in a filter. From the copper powder fraction present, further classifying steps were carried out to produce an ultrafine copper powder having a $d_{powder,50}$ particle size of <10 µm, from which an ultrafine copper powder having a $d_{powder,10}$ of 1.2 µm, and a $d_{powder,50}$ of 3 µm, and a $d_{powder,90}$ of 4.4 µm, and also a $d_{powder,98}$ of 7 µm, was produced.

b) Milling

The wet milling of the ultrafine copper powder produced in accordance with step 3a) was carried out in the same way as in example 1c.

Comparative Example 4

Commercial traded gold bronze pigment powder for gravure and flexographic printing inks ("Rotoflex" from Eckart GmbH) is produced by the known multistage dry milling process (Hametag process) using stearic acid as grinding assistant. The starting material used was a brass powder with 70% by weight copper and 30% by weight zinc, having an average particle diameter $d_{powder,50}$ of 140 µm. The leafing gold bronze pigments in the form of classified milled material, having an average particle diameter $d_{50}$=8 µm, were used to produce a gold bronze pigment having nonleafing properties, by means of subsequent surface modification with 2.5% of citric acid.

Comparative Example 5

Commercially available PVD pigment Metalure A (Eckart GmbH, Germany).

This pigment is present in the commercially available printing ink ("Ultrastar" from Eckart) for gravure and flexographic printing.

This printing ink further comprises a yellow and an orange toner dye, in order to evoke a gold color.

To determine the particle thicknesses, samples of inventive example 1 and of comparative examples 4 and 5 were characterized by means of a field ion scanning electron microscope.

For determining the thickness distribution by means of SEM, the samples were prepared as follows:

The platelet-shaped brass pigments produced from wet-milled brass powder, and present in the form of a paste or filter cake, were washed with acetone and subsequently dried.

A resin customary in electron microscopy, an example being Tempfix (Gerhard Neubauer Chemikalien, D-48031 Munster, Germany), was applied to a sample plate and heated on a hotplate until it softened. The sample plate was then removed from the hotplate and the brass powder was scattered onto the softened resin. As a result of cooling, the resin resolidified and the scattered brass pigments could be prepared in such a way that they were fixed on the sample plate standing almost vertically, by virtue of the interaction between adhesion and gravity. As a result, the brass pigments can be measured well from the side in the electron microscope. In the measurement of the thickness, the azimuthal angle of the pigment to a plane normal to the surface was estimated, and was taken into account for the thickness evaluation in accordance with the formula $$h_{eff} = h_{meas}/\cos \alpha.$$

The cumulative undersize distribution curve was plotted from the calculated $h_{eff}$ values by means of the relative frequencies. 50 to 100 particles are counted in each case.

The cumulative undersize distributions of the thickness distribution of the samples of inventive example 1 and of comparative examples 4 and 5 are shown in FIG. 1. The measurement values were each fitted with a log normal function. Distinctly apparent are the much smaller particle thicknesses of the overall particle distributions of the samples of inventive example 1, in comparison to the samples of comparative examples 4 and 5.

Tab. 1 below shows the physical characteristics of the inventive brass pigments (example 1) in comparison to commercially traded gold bronze pigment powder (comparative example 4) from Eckart and to the PVD aluminum pigment (comparative example 5) from Eckart, on the basis of the $d_{10}$, $d_{50}$, and $d_{90}$ values, and the characteristic values $h_{10}$, $h_{50}$, and $h_{90}$, and span values of the thickness measurement that are calculated from them, from the SEM investigations. The $h_{10}$, $h_{50}$, and $h_{90}$ values were calculated with the aid of the quantile function from the original thickness count data.

The longitudinal extent d of the pigments was determined by means of a laser granulometer (Cilas 1064, Cilas, France) and the measure selected for the average longitudinal extent was, as usual, the $d_{50}$ value of the cumulative undersize distribution, in µm.

TABLE 1

Physical characterization of pigments

| Samples | Sizes | | | Thicknesses | | | Span of thickness distribution [%] | Form factor |
|---|---|---|---|---|---|---|---|---|
| | $d_{10}$ [µm] | $d_{50}$ [µm] | $d_{90}$ [µm] | $h_{10}$ [nm] | $h_{50}$ [nm] | $h_{90}$ [nm] | | |
| Example 1 | 3.5 | 8.3 | 13 | 20.2 | 26.2 | 35.8 | 0.6 | 317 |
| Example 2 | 2.9 | 8.2 | 12.6 | 13.6 | 18.3 | 25.8 | 0.67 | 448 |
| Comparative example 4 | 3.3 | 8 | 15 | 29.9 | 45.2 | 74.1 | 1 | 177 |
| Comparative example 5 | 3.5 | 10 | 17.5 | 21 | 29 | 38.7 | 0.6 | 476 |

The figures in tab. 1 show that the inventive nonleafing brass pigments of examples 1 and 2 have not only a lower average thickness $h_{50}$ but also a lower $h_{90}$ value than the "Rotoflex" stabilized leafing gold bronze pigments, from Eckart GmbH, D-90763 Furth, of comparative example 4. Surprisingly, they even have lower pigment thicknesses than the "Metalure A" PVD aluminum pigments from Eckart, from comparative example 5.

The span of the thickness distribution is comparable in the case of the inventive pigments with the PVD aluminum pigments. This was hitherto unobtainable from wet milling. The conventional gold bronze pigment from wet milling (comparative example 4) shows a significantly higher span.

It is also evident from tab. 1 that the inventive brass pigments of example 1 have a substantially narrower thickness distribution (span) than the conventional gold bronze pigments of comparative example 4. Moreover, the inventive brass pigments of examples 1 and 2 have a lower parameter $d_{90}$ than the pigments of comparative examples 4 and 5.

The cumulative undersize distributions of the thickness distribution of inventive examples 1 and 2 and of comparative examples 4 and 5 are shown in FIG. 1. Clearly apparent are the much lower particle thicknesses of the overall particle distributions of the inventive examples 1 and 2 in comparison to the commercially available gold bronze pigments of comparative example 4 and the commercially available PVD aluminum pigments of example 5. The measurement values were fitted with a log normal function in each case.

For further characterization of the inventive brass pigments, so-called reverse applications were made on transparent films. This was done by printing a Melinex 400 film (PET film, 50 µm) with a gravure ink based on a commercially traded polyvinyl butyral (PVB) and on a mixture of methoxypropanol and ethyl acetate, using a printing machine.

The pigmented film reverse applications were characterized optically by gloss measurement at 60° in accordance with DIN 67 530 (instrument: micro-TRI-gloss from Byk-Gardner, D-82538 Geretsried, Germany). Calibration took place by means of dark calibration and also a black mirror glass plate with values of 92 for 60°.

The color density was measured using a densitometer (instrument: densitometer, X-Rite, D-63263 Neu-Isenburg). Calibration took place using a white standard and the unprinted substrate at a wavelength in the yellow region.

The definition of the color density of printed specimens is as follows:

$$\text{Color density} = -lg \text{ reflectance}$$

Measurement takes place of the surfaces viewed straight on.

The optical properties, determined on the basis of printing-machine proof prints (printing machine: Rotova 300, Rotocolor, 3 ink units; printing speed 75 m/min, viscosity 15 s DIN 4 flow cup, 60, 70, 80, and 90 lines/cm; level of pigmentation 25%), of film reverse applications pigmented with inventive brass pigments from example 1 and conventional gold-bronze pigments from comparative example 4, and also with tinted, conventional PVD aluminum pigments from comparative example 5, are shown in tab. 2 below.

In the case of comparative example 5, the printing ink Ultrastar (Eckart) with two different concentrations of a mixture of yellow (Yellow 79) and orange (Solvent Orange 41) dyes was used (examples 5a and 5b). The dyes were mixed in the form of the UltraStar toner series (UltraStar Toner TY-21 and TO-11; Eckart), the toner series comprising in each case dispersions of the dyes in methoxypropanol.

TABLE 2

Optical characterization, pigments I

| Sample | Gloss (60°) | | | | Color density | | | |
|---|---|---|---|---|---|---|---|---|
| | 60 l/cm | 70 l/cm | 80 l/cm | 90 l/cm | 60 l/cm | 70 l/cm | 80 l/cm | 90 l/cm |
| Example 1 | 500 | 488 | 440 | 428 | 1.45 | 1.44 | 1.32 | 1.22 |
| Comparative example 4 | 243 | 246 | 232 | 230 | 1.00 | 1.00 | 0.84 | 0.77 |
| Comparative example 5a (tinted with 35% toner) | 415 | 408 | 405 | 396 | 1.50 | 1.52 | 1.50 | 1.44 |
| Comparative example 5b (tinted with 59% toner) | 210 | 207 | 208 | 209 | 1.48 | 1.86 | 1.94 | 1.80 |

Tab. 2 shows that the film reverse applications comprising the inventive brass pigments from example 1 have a higher gloss, for all of the printing variants, than the film reverse applications pigmented with conventional pigments from comparative examples 4 and 5.

Relative to comparative example 4, moreover, the applications of the inventive pigments from example 1 have a higher color density.

The gloss of the film reverse applications of example 1 was likewise higher than for comparative examples 5a and 5b. The higher color densities of comparative examples 5a and 5b, however, suggest a greater coloredness of these applications than for example 1. In actual fact, however, this was not the case.

The visual assessment of the mirror effect of the film reverse applications gave the following results:
Example 1: clear, very good mirror
Example 4: mirror matt, hazy
Example 5a: weakly colored, silvery mirror
Example 5b: matt mirror For further optical characterization, the lightnesses, the chroma, and the hue angle of the pigmented film reverse applications were determined, with the experimental results recorded in tab. 3 below. Lightness measurements were carried out using a commercially available instrument from X-Rite (light source D65, 10° standard observer) in diffuse measurement geometry, with an observation angle of 8°. In this case, as an example, the values at 60 l/cm were measured.

The chroma C* recorded in tab. 3 describes the relative saturation in relation to the reference white, in other words in comparison to a defined lightest point in a color space. The hue angle h*, which is likewise recorded in tab. 3, is the color value assigned to the color shade, which is also identified as hue.

TABLE 3

Optical characterization of pigments II, diffuse measurement geometry

| Sample | L* | a* | b* | c* | H* | Gloss (60°) 60 l/cm |
|---|---|---|---|---|---|---|
| Example 1 | 84.5 | 3.0 | 31.5 | 31.6 | 84.5 | 500 |
| Comparative example 4 | 78.8 | 3.6 | 27.9 | 28.2 | 82.7 | 243 |
| Comparative example 5a (tinted with 35% toner) | 83.8 | 0.0 | 10.2 | 10.2 | 89.8 | 415 |
| Comparative example 5b (tinted with 59% toner) | 77.2 | 0.2 | 27.4 | 27.4 | 89.5 | 210 |

From tab. 3 it is apparent that the inventive brass pigments from example 1 were more intensely colored than those of comparative examples 4 and 5. These measurements also corresponded much more to the visual impression.

This means that the gold bronze pigment from example 1, on account of its low pigment thickness, possessed a high gloss (luster) and also, owing to its inherent color, a high color value (chroma). It is also evident from tab. 3 that the optical properties of the toner-tinted film reverse applications from examples 5a and 5b correlated with the amount of toner used as tinting agent. Hence the film reverse applications from example 5b, which contained more tinting agent (toner), did give a higher chroma (C*), but gave lower lightnesses L* and a substantially reduced gloss (60°) than the film reverse applications of example 5a, containing a lower level of tinting agent (toner). Evidently, the color pigments scatter the light too much and so reduce the metallic effect. These disadvantages can be overcome with the inventive metallic effect pigments.

As a further criterion for assessment, the adhesive strength of the pigmented reverse applications was determined by means of an adhesive-tape test (splitting resistance).

For this purpose, an adhesive strip was adhered firmly and without bubbles to the surface. This adhesive strip was then peeled off again, so that the substrate was not damaged. The splitting resistance was assessed on the basis of a rating system, visually, from rating 1 (very good) to rating 5 (very poor). A poor splitting resistance is reflected in a correspondingly high level of extraction from the print.

It was found that the inventive brass pigments from example 1 had a better adhesive strength (rating 2) than the gold bronze pigments from comparative example 4 (rating 4) and the PVD aluminum pigments from comparative example 5 (rating 3).

For the pigmentation of aqueous applications, such as printing inks, for example, the inventive brass pigments may be provided with a protective layer that entirely surrounds the pigment surface. In example 6 below, the production of a brass pigment coated with $SiO_2$ is described.

Example 6

55.1 g of a paste with brass pigments according to example 1 (corresponding to 38.6 g of brass) were dispersed in 375 ml of isopropanol and this dispersion was brought to boiling temperature. 4.75 g of tetraethoxysilane were added. Subsequently, over a time period of 3 hours, a solution of 4 g of 25% $NH_3$ in 5 g of water were metered in. After a further 3 hours, the suspension was cooled to room temperature and filtered off with suction on a Buchner funnel. The product was then dried overnight in a vacuum dryer at 100° C.

The pigments gave very good results in the $H_2S$ exposure test. Additionally, the pigments were incorporated into various aqueous printing ink systems. In these systems, agglomeration phenomena and/or green colorations were obtained in some cases not at all and in some cases at levels at no more than those observed with otherwise customary, passivated gold bronze pigments (pigments of the Dorolan® series, Eckart).

Green colorations and agglomerations are attributable to copper ions and zinc ions that form, respectively.

When the experimental results are viewed as a whole, it is notable that the inventive pigments exhibit pigment characteristics, particularly in respect of thickness, thickness distribution, and opacity, that have not hitherto been achieved with conventional leafing gold bronze pigments produced by dry milling. The film reverse applications pigmented with inventive pigments are notable for attractive coloristic properties, especially for a gold mirror effect with a high color density, which it has not hitherto been possible to achieve with PVD aluminum pigments containing color pigments. Film reverse applications pigmented with inventive pigments possess a high adhesive strength. Moreover, as a result of the high opacity of the inventive pigments, it is possible to reduce the amount in which they are used in the application medium.

What is claimed is:

1. Platelet-shaped, copper-containing, metallic effect pigments which have a copper content of 60% to 100% by weight, based on the total metal content, wherein the metallic effect pigments have a thickness distribution as determined via thickness counting by scanning electron microscopy (SEM) and represented as cumulative undersize distribution,
   a) with an $h_{50}$ of 10 to 50 nm, and
   b) with an $h_{90}$ of 20 to 70 nm,
   the platelet-shaped, copper-containing, metallic effect pigments being produced by milling a copper-containing metal powder with lubricant.

2. The platelet-shaped, copper-containing, metallic effect pigments as claimed in claim 1, wherein the pigments have an $h_{50}$ of 15 to 45 nm.

3. The platelet-shaped, copper-containing, metallic effect pigments as claimed in claim 1, wherein the pigments have an $h_{90}$ of 20 to 60 nm.

4. The platelet-shaped, copper-containing, metallic effect pigments as claimed in claim 1, wherein the pigments have an $h_{98}$ of 21 to below 80 nm.

5. The platelet-shaped, copper-containing, metallic effect pigments as claimed in claim 1, wherein the pigments have an $h_{10}$ of 8 to 25 nm.

6. The platelet-shaped, copper-containing, metallic effect pigments as claimed in claim 1, wherein the pigments have a relative breadth of the thickness distribution $\Delta h$, as determined via thickness counting by scanning electron microscopy (SEM), which is calculated from a corresponding cumulative undersize curve of a relative frequency according to the formula $\Delta h = 100 \times (h_{90} - h_{10})/h_{50}$, of 30% to 90%.

7. The platelet-shaped, copper-containing, metallic effect pigments as claimed in claim 1, wherein the pigments have an average size $d_{50}$ in the range from 3 to 50 µm.

8. The platelet-shaped, copper-containing, metallic effect pigments as claimed in claim 1, wherein the pigments have a form factor $d_{50}/h_{50}$ in the range from 150 to 3000.

9. The platelet-shaped, copper-containing, metallic effect pigments as claimed in claim 1, wherein the pigments have nonleafing properties.

10. The platelet-shaped, copper-containing, metallic effect pigments as claimed in claim 9, wherein a surface of the pigments is covered at least partly with an additive, the additive comprising, as structural units, at least one carboxylic acid having at least 4 carbon atoms, and at least one polyglycol ether, the carboxylic acid and the polyglycol ether being bonded covalently to one another.

11. The platelet-shaped, copper-containing, metallic effect pigments as claimed in claim 1, wherein the pigments are coated with at least one of a passivating inhibitor layer and an anticorrosion layer.

12. The platelet-shaped, copper-containing, metallic effect pigments as claimed in claim 1, wherein the pigments are present as powder or paste.

13. The platelet-shaped, copper-containing, metallic effect pigments as claimed in claim 12, wherein the pigments are present as paste used in forming at least one selected from the group consisting of gravure, flexographic and screen printing inks.

14. A process for producing platelet-shaped, copper-containing, metallic effect pigments as claimed in claim 1 by milling, said process comprising the following step:
    milling a copper-containing metal powder having a particle size distribution with a $d_{Powder,50}$ of 1 to 15 µm and a $d_{Powder,90}$ of 2 to 27 µm and a copper content of 60% to 100% by weight, based on the total metal powder, to form platelet-shaped, metallic effect pigments, using a milling apparatus, in the presence of lubricants and grinding media and optionally solvent, wherein the copper-containing metal powder has a span $\Delta d_{powder} = (d_{powder,90} - d_{powder,10})/d_{powder,50}$ of 0.8 to 1.7, the resultant platelet-shaped metallic effect pigments having an average thickness as determined by thickness counting by scanning electron microscopy (SEM) with an $h_{50}$ of 10 to 50 nm and an $h_{90}$ of 20 to 70 nm.

15. The process as claimed in claim 14, wherein the copper-containing metal powder is milled over a period of 10 to 100 hours.

16. The process as claimed in claim 14, wherein an additive is used as lubricant, the additive comprising, as structural units, at least one carboxylic acid having at least 4 carbon atoms, and at least one polyglycol ether, the carboxylic acid and the polyglycol ether being bonded covalently to one another.

17. A coating composition comprising platelet-shaped, copper-containing, metallic effect pigments as claimed in claim 1.

18. A coating composition as claimed in claim 17 wherein the composition is a printing ink.

19. A coated article whose coating comprises the platelet-shaped, copper-containing, metallic effect pigments as claimed in claim 1.

* * * * *